(12) United States Patent
Vahle et al.

(10) Patent No.: US 11,958,356 B2
(45) Date of Patent: Apr. 16, 2024

(54) MULTI-JURISDICTIONAL REQUIREMENT SORTING SYSTEM FOR COMPLIANCE DEVICES

(71) Applicant: Consumer Safety Technology, LLC, Des Moines, IA (US)

(72) Inventors: Gretchen T. Vahle, San Diego, CA (US); Melissa Cole Ray, Granbury, TX (US); Amanda Renee Mallinger, Des Moines, IA (US)

(73) Assignee: Consumer Safety Technology, LLC, Des Moines, IA (US)

( * ) Notice: Subject to any disclaimer, the term of this patent is extended or adjusted under 35 U.S.C. 154(b) by 0 days.

(21) Appl. No.: 18/199,347

(22) Filed: May 18, 2023

(65) Prior Publication Data

US 2023/0373297 A1 Nov. 23, 2023

Related U.S. Application Data

(60) Provisional application No. 63/344,365, filed on May 20, 2022.

(51) Int. Cl.
*B60K 28/06* (2006.01)
*A61B 5/08* (2006.01)
*B60W 40/08* (2012.01)

(52) U.S. Cl.
CPC ............ *B60K 28/063* (2013.01); *A61B 5/082* (2013.01); *B60W 40/08* (2013.01); *B60W 2040/0818* (2013.01); *B60W 2540/26* (2013.01)

(58) Field of Classification Search
None
See application file for complete search history.

(56) References Cited

U.S. PATENT DOCUMENTS

| | | | |
|---|---|---|---|
| 7,934,577 B2 | 5/2011 | DeVries et al. | |
| 8,957,771 B2 | 2/2015 | Arringdale et al. | |
| 10,604,011 B2 | 3/2020 | DeVries et al. | |
| 10,663,440 B2 | 5/2020 | DeVries | |
| 10,877,008 B2 | 12/2020 | DeVries et al. | |
| 2017/0105674 A1* | 4/2017 | Abbott | A61B 5/0022 |
| 2020/0215912 A1 | 7/2020 | DeVries et al. | |
| 2021/0182870 A1 | 6/2021 | Degeneffe et al. | |

* cited by examiner

*Primary Examiner* — Thomas S McCormack
(74) *Attorney, Agent, or Firm* — Pauly, DeVries Smith & Deffner LLC

(57) ABSTRACT

A method includes receiving criteria data regarding a first control requirement frame for a first jurisdiction, a second control requirement frame for a second jurisdiction, and a third control requirement frame for a third jurisdiction. The criteria data for each control requirement frame includes at least: i. criteria data for an intoxicant concentration limit data subframe; ii. criteria data for a calibration requirement data subframe; and iii. criteria data for a reporting subframe. The method further includes storing the criteria data in a stringency database; sorting the first, second and third control requirement frames based on the relative stringency of criteria data. receiving a request for a compliance device according to the requirements of the first jurisdiction and the second jurisdiction; accessing the sorted control frames of the first and second jurisdictions to determine an operational control frame based on the sorted control frames; and providing the operation control frame.

19 Claims, 12 Drawing Sheets

| | Control Requirement #1 | Score For Req. #1 | Control Requirement #2 | Score For Req. #2 | Control Requirement #3 | Score For Req. #3 | Control Requirement #4 | Score For Req. #4 | Control Requirement #5 | Score For Req. #5 | Control Requirement #6 | Score For Req. #6 | Score Total |
|---|---|---|---|---|---|---|---|---|---|---|---|---|---|
| Controlling Data | Criteria Data 1/1 | | Criteria Data 1/2 | | Criteria Data 2/3 | | Criteria Data 1/4 | | Criteria Data 1/5 | | Criteria Data 1/6 | | |
| Jurisdiction #1 | Criteria Data 1/1 | 4 | Criteria Data 1/2 | 1 | Criteria Data 1/3 | 0 | Criteria Data 1/4 | 3 | Criteria Data 1/5 | 2 | Criteria Data 1/6 | 2 | 12 |
| Jurisdiction #2 | Criteria Data 2/1 | 3 | Criteria Data 2/2 | 1 | Criteria Data 2/3 | 1 | Criteria Data 2/4 | 1 | Criteria Data 2/5 | 2 | Criteria Data 2/6 | 2 | 10 |
| Jurisdiction #3 | Criteria Data 3/1 | 4 | Criteria Data 3/2 | 0 | Criteria Data 3/3 | 1 | Criteria Data 3/4 | 1 | Criteria Data 3/5 | 1 | Criteria Data 3/6 | 2 | 9 |
| Jurisdiction #4 | Criteria Data 4/1 | 3 | Criteria Data 4/2 | 1 | Criteria Data 4/3 | 0 | Criteria Data 4/4 | 0 | Criteria Data 4/5 | 2 | Criteria Data 4/6 | 2 | 8 |
| Jurisdiction #5 | Criteria Data 5/1 | 4 | Criteria Data 5/2 | 1 | Criteria Data 5/3 | 0 | Criteria Data 5/4 | 1 | Criteria Data 5/5 | 0 | Criteria Data 5/6 | 0 | 6 |
| Jurisdiction #6 | Criteria Data 6/1 | 2 | Criteria Data 6/2 | 0 | Criteria Data 6/3 | 1 | Criteria Data 6/4 | 0 | Criteria Data 6/5 | 1 | Criteria Data 6/6 | 2 | 6 |
| Jurisdiction #7 | Criteria Data 7/1 | 2 | Criteria Data 7/2 | 0 | Criteria Data 7/3 | 1 | Criteria Data 7/4 | 0 | Criteria Data 7/5 | 0 | Criteria Data 7/6 | 2 | 5 |
| Jurisdiction #8 | Criteria Data 8/1 | 3 | Criteria Data 8/2 | 1 | Criteria Data 8/3 | 0 | Criteria Data 8/4 | 0 | Criteria Data 8/5 | 0 | Criteria Data 8/6 | 0 | 4 |

FIG. 7

| Controlling Data | BAC Threshold | Score | GPS | Score | Camera | Score | Allow Out of State Servicing | Score | Number of Dirty Samples During Calibration | Score | Technician Name Required | Score | Total Score |
|---|---|---|---|---|---|---|---|---|---|---|---|---|---|
| AL | 0.021 | | Required | | Required | | No - CA only | | 2 | | Yes | | |
| AK | 0.025 | 2 | Required | 1 | Required | 1 | Yes | 0 | 2 | 2 | Yes | 1 | 7 |
| AZ | 0.02 | 3 | Not Allowed | 1 | Required | 1 | No | 1 | 1 | 1 | No | 0 | 7 |
| AR | 0.015 | 4 | Required | 1 | Required | 1 | No | 1 | 1 | 1 | No | 0 | 8 |
| CA | 0.02 | 3 | Silent | 0 | Not Allowed | 0 | Yes | 0 | 2 | 2 | Yes | 1 | 6 |
| CO | 0.021 | 2.5 | Required | 1 | Required | 1 | No | 1 | 2 | 2 | Yes | 1 | 8.5 |
| CT | 0.021 | 2.5 | Required | 1 | Required | 1 | No | 1 | 1 | 1 | Yes | 1 | 7.5 |
| DE | 0.02 | 3 | Silent | 0 | Required | 1 | Yes | 1 | 2 | 2 | Yes | 1 | 7 |
| | 0.021 | 2.5 | Required | 1 | Required | 1 | Yes | 1 | 1 | 1 | No | 0 | 5.5 |

FIG. 8

| | BAC Threshold | Score | GPS | Score | Camera | Score | Allow Out of State Servicing | Score | Number of Dirty Samples During Calibration | Score | Technician Name Required | Score | Total Score |
|---|---|---|---|---|---|---|---|---|---|---|---|---|---|
| Controlling Data | 0.021 | | Required | | Required | | No - CO only | | 1 | | Yes | | |
| AL | 0.025 | 2 | Required | 1 | Required | 1 | Yes | 0 | 2 | 1 | Yes | 1 | 7 |
| AK | 0.02 | 3 | Not Allowed | 1 | Required | 1 | No | 1 | 1 | 1 | No | 0 | 7 |
| AZ | 0.015 | 4 | Required | 1 | Required | 1 | No | 1 | 1 | 1 | No | 0 | 8 |
| AR | 0.02 | 3 | Silent | 0 | Not Allowed | 0 | Yes | 0 | 2 | 1 | Yes | 1 | 6 |
| CA | 0.021 | 2.5 | Required | 1 | Required | 1 | No | 1 | 2 | 1 | Yes | 1 | 8.5 |
| CO | 0.021 | 2.5 | Required | 1 | Required | 1 | No | 1 | 1 | 1 | Yes | 1 | 7.5 |
| CT | 0.02 | 3 | Silent | 0 | Required | 1 | Yes | 0 | 2 | 1 | Yes | 1 | 7 |
| DE | 0.021 | 2.5 | Required | 1 | Required | 1 | Yes | 0 | 1 | 1 | No | 0 | 5.5 |

FIG. 9

| | BAC Threshold | Score | GPS | Score | Camera | Score | Allow Out of State Servicing | Score | Number of Dirty Samples During Calibration | Score | Technician Name Required | Score | Total Score |
|---|---|---|---|---|---|---|---|---|---|---|---|---|---|
| Controlling Data | 0.021 | | Required | | Required | | No - CO only | | 2 | | Yes | | |
| AL | 0.025 | 2 | Required | 1 | Required | 1 | Yes | 0 | 2 | 2 | Yes | 1 | 7 |
| AK | 0.02 | 3 | Not Allowed | 1 | Required | 1 | No | 1 | 1 | 1 | No | 0 | 7 |
| AZ | 0.015 | 4 | Required | 0 | Required | 1 | No | 1 | 1 | 1 | No | 0 | 8 |
| AR | 0.02 | 3 | Silent | 1 | Not Allowed | 0 | Yes | 0 | 2 | 2 | Yes | 1 | 6 |
| CA | 0.021 | 2.5 | Required | 1 | Required | 1 | No | 1 | 2 | 2 | Yes | 1 | 8.5 |
| CO | 0.021 | 2.5 | Required | 1 | Required | 1 | No | 1 | 1 | 1 | Yes | 1 | 7.5 |
| CT | 0.02 | 3 | Silent | 0 | Required | 1 | Yes | 0 | 2 | 2 | Yes | 1 | 7 |
| DE | 0.021 | 2.5 | Required | 1 | Required | 1 | Yes | 0 | 1 | 1 | No | 0 | 5.5 |

FIG. 10

MULTI-JURISDICTIONAL REQUIREMENT SORTING SYSTEM FOR COMPLIANCE DEVICES

This application claims the benefit of U.S. Provisional Application No. 63/344,365, filed May 20, 2022, the content of which is herein incorporated by reference in its entirety.

FIELD

Embodiments herein relate to systems and methods for providing vehicle immobilization systems that conform to the requirements of multiple jurisdictions and report to multiple jurisdictions.

BACKGROUND

Vehicles incorporate breath alcohol ignition interlock devices, sometimes abbreviated as BAIIDs, to prevent a driver with a known history of driving while intoxicated with alcohol from operating the vehicle while intoxicated. Such devices are designed to prevent a driver from starting a motor vehicle when the driver's breath alcohol concentration (BrAC) is at or above a set alcohol concentration.

In operation, a driver uses a BAIID device by blowing into an alcohol-sensing element, such as a fuel cell, that measures the amount of alcohol in the driver's breath. The BAIID reads a signal from the fuel cell or other alcohol-sensing element and determines whether the driver's blood alcohol content exceeds a threshold amount, based on a known relationship between blood alcohol and breath alcohol. If the driver's determined blood alcohol content does not exceed the threshold, the BAIID allows the vehicle to start and run by electrically enabling a system within the vehicle, such as the starter, fuel pump, ignition, or the like. If the driver's blood alcohol concentration exceeds the threshold, the vehicle is not allowed to start, and the BAIID device records the event.

Each state in the U.S. has adopted a law providing for use of such BAIID devices as a sanction for drivers convicted of driving while intoxicated, or as a condition of restoring some driving privileges after such offenses. Many other territories and countries around the world have these types of laws. In some instances, multiple jurisdictions (e.g. states) can have an interest in a subject using a BAIID or require a subject to use a BAIID However, since each jurisdiction can have its own rules and regulations for a BAIID, compliance to each jurisdiction can be difficult.

SUMMARY

Various embodiments provide a method including receiving, at a non-transitory computer memory, criteria data regarding a first control requirement frame for a first jurisdiction, a second control requirement frame for a second jurisdiction, and a third control requirement frame for a third jurisdiction. The criteria data for each control requirement frame includes at least: criteria data for an intoxicant concentration limit data subframe, criteria data for a calibration requirement data subframe, and criteria data for a reporting subframe. The method further includes storing the criteria data in a stringency database, sorting the first, second and third control requirement frames based on the relative stringency of criteria data. receiving a request for a compliance device according to the requirements of the first jurisdiction and the second jurisdiction, accessing the sorted control frames of the first and second jurisdictions to determine an operational control frame based on the sorted control frames, and providing the operation control frame.

In various embodiments, sorting the first, second and third control requirement frames includes evaluating the intoxicant concentration limit data subframes relative to each other, evaluating the calibration requirement data subframes relative to each other, and evaluating the reporting subframes relative to each other.

In various embodiments, the criteria data for each control requirement frame includes a compliance device service location subframe or a compliance device service personnel subframe.

In various embodiments, the method can further include electronically sending instructions for preparing the compliance device in accordance with the operational control frame.

In various embodiments, the method can further include preparing firmware for the compliance device in accordance with the operational control frame.

In various embodiments, the method can further include electronically sending the firmware to the compliance device.

In various embodiments, the method can further include electronically sending the firmware to a transfer device, wherein the transfer device is configured to configure the firmware of the compliance device.

In various embodiments, the transfer device includes a calibration station, wherein the calibration station is configured to calibrate the compliance device and communicate with a non-transitory computer memory of the compliance device.

In various embodiments, the intoxication concentration limit data is selected from the group consisting of an alcohol concentration limit, a tetrahydrocannabinol (THC) concentration limit, and an alcohol concentration limit and a tetrahydrocannabinol (THC) concentration limit.

In various embodiments, the compliance device includes an ignition interlock device.

In various embodiments, the ignition interlock device includes a breath alcohol ignition interlock device.

In various embodiments, the method can further include receiving test event data from the compliance device in response to a testing event.

In various embodiments, the method can further include preparing a first report for one of the at least two jurisdictions, can include a common portion of the test event data and a unique portion of the test event data, preparing a second report for a second of the at least two jurisdictions can include the common portion of the test event data, wherein the second report does not include the unique portion of the test event data so that the first report differs from the second report, and sending the first report to at least one of the jurisdictions, and m. sending the second report to at least one of the jurisdictions.

In various embodiments, the testing event data includes an intoxicant concentration value from a biological sample provided to the compliance device.

In various embodiments, the biological sample includes a breath sample, a saliva sample, a blood sample, or a urine sample.

In various embodiments, the compliance device is configured to receive a biological sample, and wherein the compliance device is further configured to analyze the biological sample and to determine an intoxicant concentration.

In various embodiments, providing the operation control frame includes sending hardware data to a remote computing device, wherein the hardware data is defined by the operational control frame.

In various embodiments, the hardware data includes instructions for preparing the compliance device.

Various embodiments provide a method that includes receiving, at a non-transitory computer memory, criteria data regarding a first control requirement frame for a first jurisdiction, a second control requirement frame for a second jurisdiction, and a third control requirement frame for a third jurisdiction. The criteria data for each control requirement frame includes at least: i. criteria data for an alcohol concentration limit data subframe, ii. criteria data for a calibration requirement data subframe, and iii. criteria data for a reporting subframe. The method can further include storing the criteria data in a stringency database, sorting the criteria data within each subframe based on the relative stringency of criteria data, receiving a request for a compliance device that complies with the first jurisdiction and the second jurisdiction, and accessing the sorted criteria data within each subframe of the first and second jurisdictions to determine control criteria data for a combined control requirement frame for the compliance device. The control criteria data includes the criteria data of a more stringent jurisdiction for each subframe. The control criteria data includes at least a portion of the criteria data for the first jurisdiction and a portion of the criteria data for the second jurisdiction. The method can further include providing the combined control requirement frame for the compliance device.

Various embodiments provide a system having a non-transitory computer memory and a computer processor. The system can further include computer instructions stored on the memory for instructing the processor to perform the step of: receiving, at a non-transitory computer memory, criteria data regarding a first control requirement frame for a first jurisdiction, a second control requirement frame for a second jurisdiction, and a third control requirement frame for a third jurisdiction. The criteria data for each control requirement frame includes at least: i. criteria data for an intoxicant concentration limit data subframe, ii. criteria data for a calibration requirement data subframe, and iii. criteria data for a reporting subframe. The computer instructions stored on the memory can further include instructing the processor to perform the steps of storing the criteria data in a stringency database, sorting the first, second and third control requirement frames based on the relative stringency of criteria data. receiving a request for a compliance device according to the requirements of the first jurisdiction and the second jurisdiction, accessing the sorted control frames of the first and second jurisdictions to determine an operational control frame based on the sorted control frames, and providing the operation control frame.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which:

FIG. 7 is a schematic view of criteria data in accordance with various embodiments herein.

FIG. 8 is a schematic view of criteria data in accordance with various embodiments herein.

FIG. 9 is a schematic view of criteria data in accordance with various embodiments herein.

FIG. 10 is a schematic view of criteria data in accordance with various embodiments herein.

While embodiments are susceptible to various modifications and alternative forms, specifics thereof have been shown by way of example and drawings and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

Monitoring devices, such as ignition interlock devices, portable monitoring devices, at-home monitoring devices, or other monitoring devices, can be required by a jurisdiction for a subject. In some instances, multiple jurisdictions require a subject to use an ignition interlock device or monitoring device. As an example, a first jurisdiction can issue the subject a driver's license and the subject could have been convicted of a driving while intoxicated violation in a second jurisdiction. The second jurisdiction might require the subject to use an ignition interlock device for a period of time as a repercussion of the driving while intoxicated violation. As the issuer of the subject's driver's license the first jurisdiction may also require the subject to use an ignition interlock device for a time period, such as six months. In many cases, the first jurisdiction can have different requirements for an intoxication interlock system than the second jurisdiction. For some settings or configurations of the ignition interlock, the two jurisdictions can have the same requirements, which makes configuring the device straight forward. However, in many scenarios, the first and second jurisdictions can have different requirements for at least some settings and configurations.

The systems and methods provided herein can provide resolutions to differences between requirements for different jurisdictions. The systems and methods provided herein can provide a device that complies with the requirements of both jurisdictions, or more jurisdictions, if applicable. The systems and methods provided herein can provide reports to different jurisdictions based on the requirements of each jurisdiction. The systems and methods provided herein can provide recommendations or software updates for device settings and configurations.

In some embodiments, the systems and methods provided herein can prepare a matrix or algorithm to determine which jurisdiction's requirements should control the device. In some embodiments, the systems and methods provided herein can access the matrix or algorithm to determine how the device should be configured. In some embodiments, the systems and methods provided herein can provide a device configured to the requirements of a controlling or primary jurisdiction. In some embodiments, the systems and methods provided herein can provide a device configured to the requirements of two or more jurisdictions.

Figure 1:
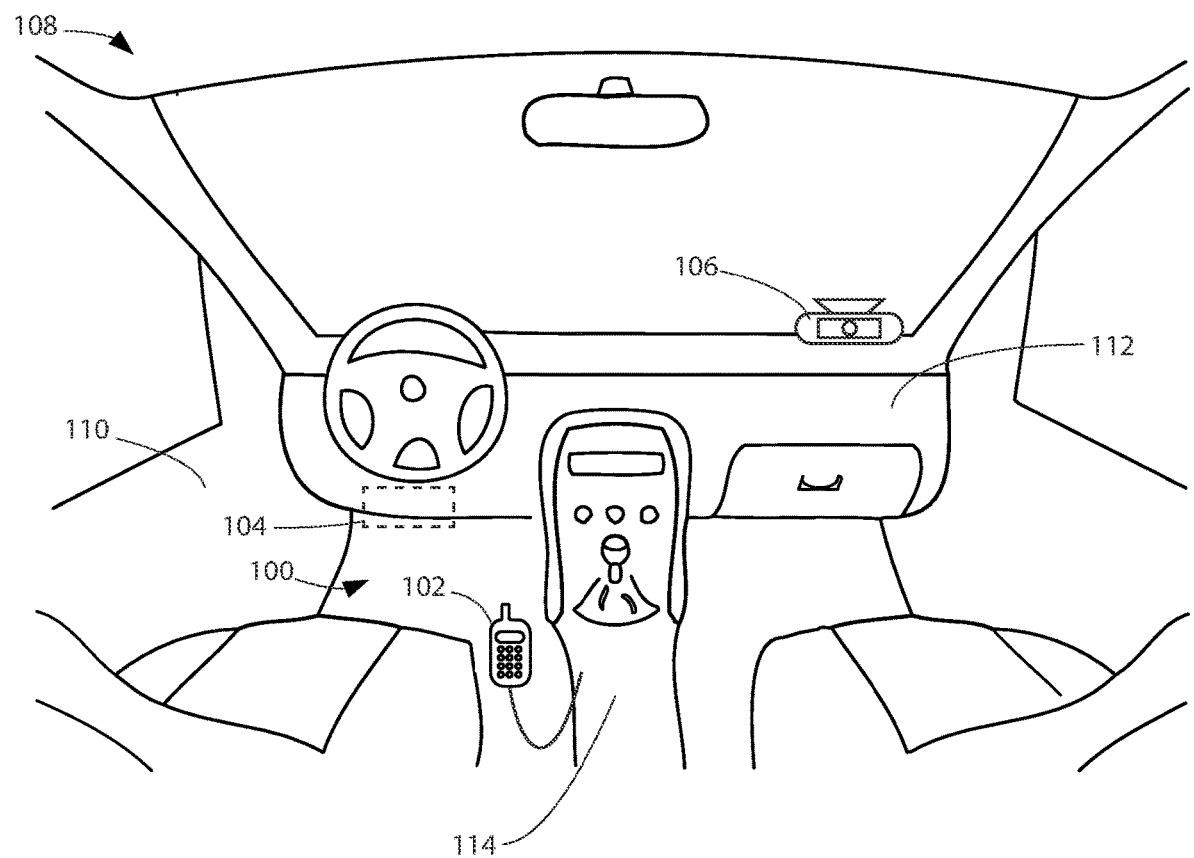
FIG. 1 is a view of the interior of a vehicle in accordance with various embodiments herein.

Referring now to FIG. 1, a portion of an interior of a vehicle 108 is shown in accordance with various embodiments herein. In various embodiments, the interior of vehicle 108 can include a driver's seat on the left, a front passenger seat on the right, a steering wheel, and other common elements of a typical vehicle interior. The vehicle further includes an ignition interlock device installed within. The ignition interlock device can be in the form of a Breath Alcohol Ignition Interlock Device (BAIID) 100 configured to selectively enable vehicle operation based on a driver's intoxication state. In various embodiments, the BAIID 100 can include one or more of a detection unit 102, a control system 104, and a camera 106. In some embodiments, the detection unit 102 is coupled to the control system 104. While interlock device of the illustrated embodiment is configured to detect alcohol, it will be appreciated that the systems and methods described herein can be used in conjunction with interlock devices that are configured to detect various intoxicants, e.g., tetrahydrocannabinol (THC), opioids, narcotics, etc.

In various embodiments, the control system 104 is configured to fit within a passenger compartment 110 of a vehicle 108, such as under or behind the dashboard 112 of the vehicle 108, within the center console 114 of the vehicle, or both. In some examples, installation of the BAIID system 100 involves mounting the control system 104 under the dashboard 112 of the vehicle 108 and coupling the detection unit 102 to the control system 104. In some embodiments, the detection unit 102, the control system 104, or both can be configured to send and/or receive data, such as to other computing devices. In some embodiments, the detection unit 102, the control system 104, or both can have wireless communication abilities. In some embodiments, the detection unit 102, the control system 104, or both can include a cellular modem to facilitate wireless communication.

The detection unit 102 can be coupled to the control system 104 via a wired connection. In an alternate embodiment, the connection between the control system 104 and the detection unit 102 is wireless, such as using radio-frequency communications. In various embodiments, the installation has only the detection unit 102 exposed in the vehicle for passenger interaction, which reduces the chance of tampering with the system 100. The control system 104 may also be connected to other vehicle systems, such as to a power source, and/or to the ignition or other systems to monitor and/or control the operating state of the vehicle.

In various embodiments, the camera 106 can be mounted on or coupled to the dashboard 112. In other embodiments, the camera 106 can be mounted on or coupled to the windshield, such as a lower portion of the windshield to reduce the risk of the camera 106 interfering with the driver's visibility out the windshield. The camera 106 can be connected to the detection unit 102, the control system 104, or both, such as to transfer data and commands. The detection unit 102, the control system 104, or both can send a request to the camera 106 to capture an image, such as when a user is submitting a breath sample. The camera 106 can send or transmit the captured image to the detection unit 102, the control system 104, or both.

Figure 2:
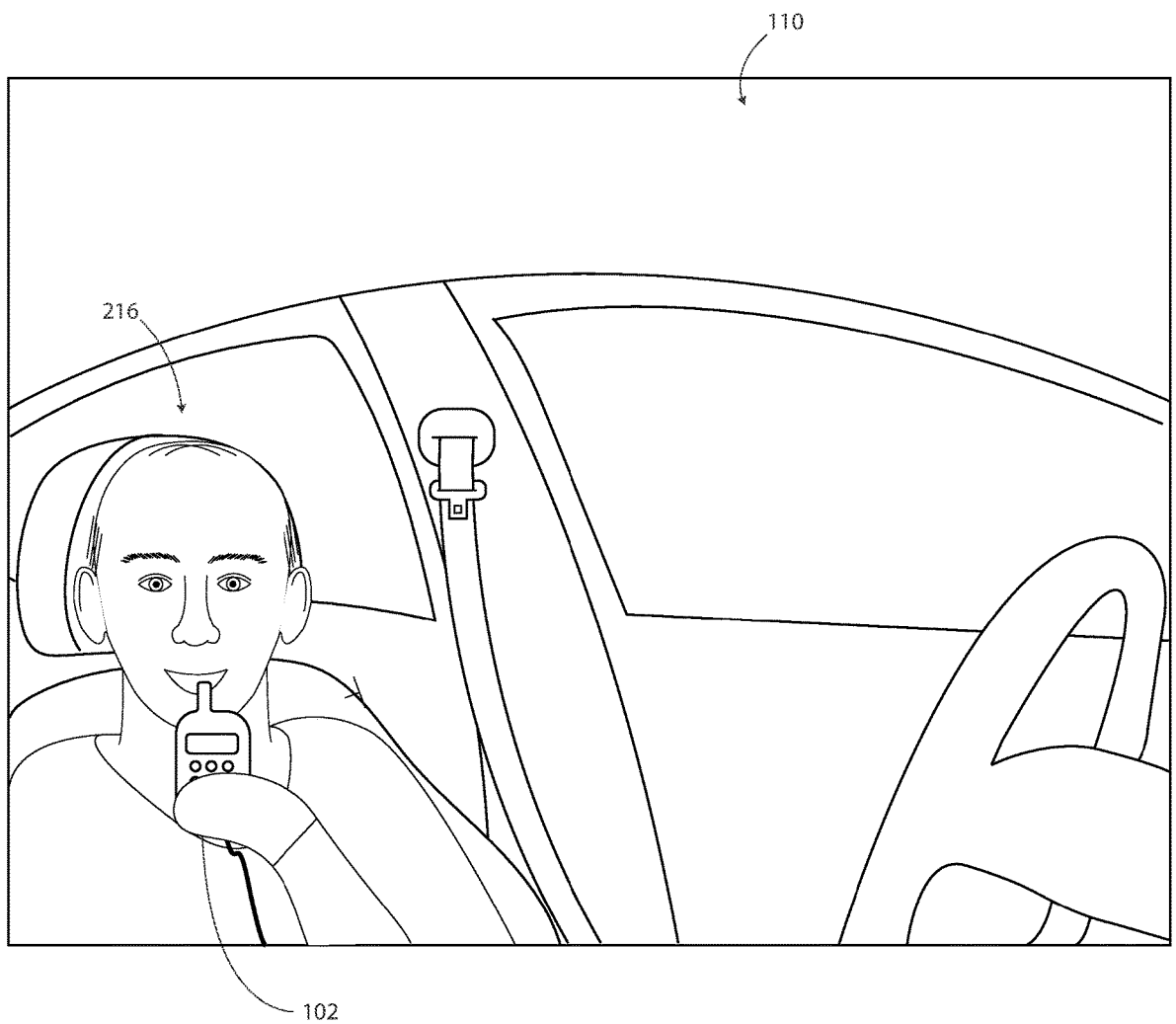
FIG. 2 is a schematic view of an image captured by an interlock device in accordance with various embodiments herein.

Referring now to FIG. 2, a schematic of an image captured by the camera 106 is shown in accordance with various embodiments herein. As mentioned above, in use, a subject 216 provides a breath sample, such as a deep lung sample, to the detection unit 102. The detection unit 102, in some embodiments along with the control system 104, can determine the subject's alcohol concentration, such as by determining the subject's blood alcohol concentration based on the subject's breath alcohol concentration.

The image shown in FIG. 2 shows the passenger compartment 110 with a subject 216 providing a breath sample into the detection unit 102. In various embodiments, the camera 106 can be configured to capture the subject's face and the detection unit 102 during a test event. The image can be referenced to determine if a valid sample was provided.

Figure 3:
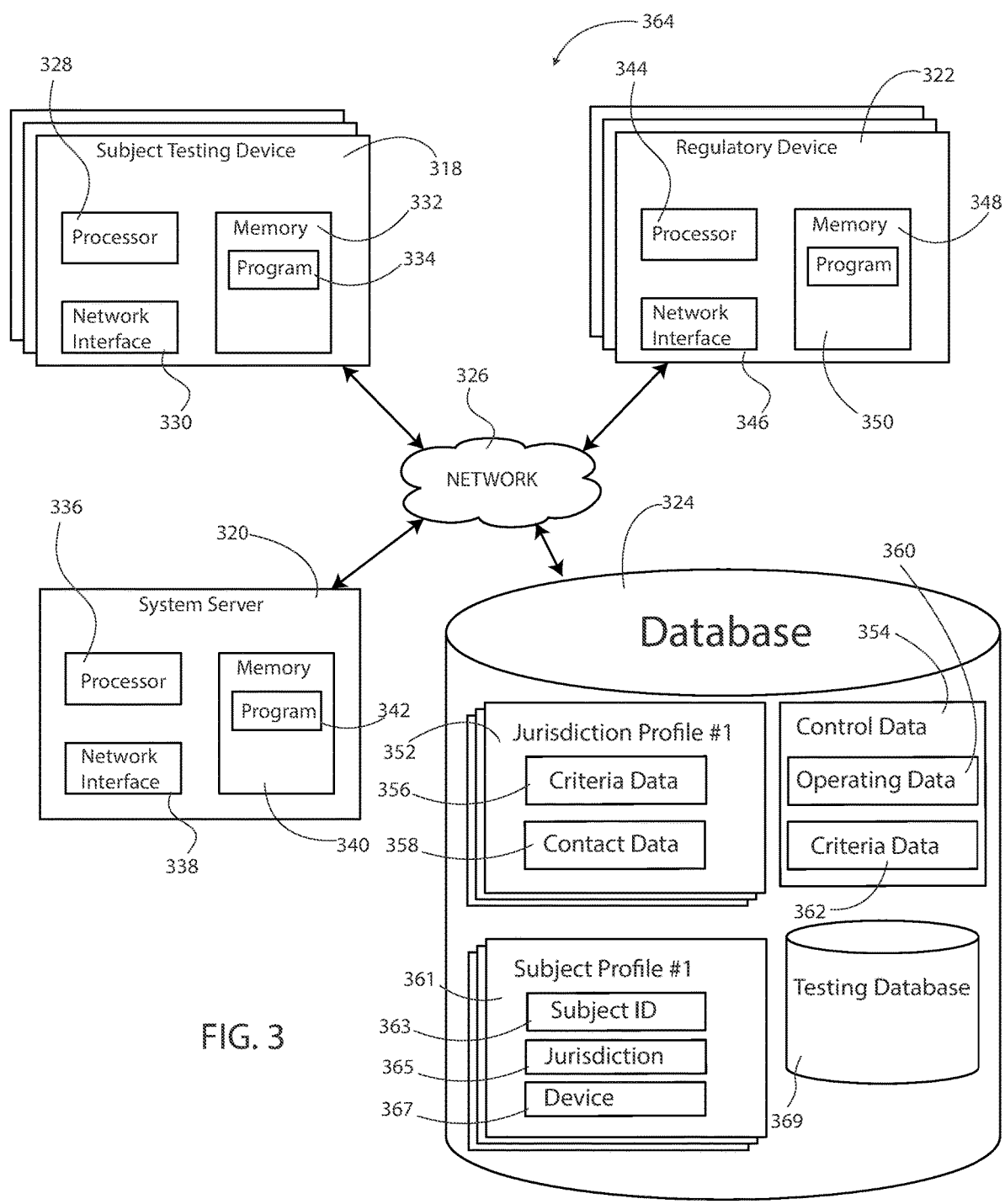
FIG. 3 is a schematic view of various components of a system in accordance with various embodiments herein.

FIG. 3 is a schematic view of various components of a system in accordance with various embodiments herein. FIG. 3 shows a schematic of the system 364 that can be used to determine the devices settings and configurations to comply with multiple jurisdictions. The system 364 can also receive, store, process, transfer, and present data related to intoxicant monitoring of various subjects. The data recorded by the subject testing device 318, such as BAIID 100, can be managed in part by a system server 320 and stored in a database 324, such as a testing database within the database 324. Data, such as the recorded data or a summary of the recorded data, can be reported to or sent to one or more regulatory devices 322. In some embodiments, a regulatory device 322 can access data on the system server 320 through the network 326. The database 324 can store additional data created by or received from the system server 320, the subject testing device 318, and the regulatory device 322.

Various subject test devices 318 are disclosed in U.S. Pat. No. 10,604,011, titled "NETWORK INTOXICATION VEHICLE IMMOBILIZATION," issued on Mar. 31, 2020, which is hereby incorporated by reference in its entirety, U.S. Pat. No. 7,934,577, titled "IGNITION INTERLOCK BREATHALYZER" issued on May 3, 2011, which is hereby incorporated by reference in its entirety, and U.S. Pat. No. 8,957,771, titled "APPARATUS, SYSTEM, AND METHOD FOR IMPLEMENTING AND MONITORING BREATH ALCOHOL TESTING PROGRAMS, USUALLY FROM A FIXED POINT LOCATION, SUCH AS A HOME" issued on Feb. 17, 2015, which is hereby incorporated by reference in its entirety.

The system 364 shown in FIG. 3 can include a subject testing device 318, a system server 320, and a regulatory device 322. These devices 318, 320, 322 can be computer systems or include computer systems. In various embodiments, these computing systems can each include a processor 328, 336, 344, memory and/or storage 332, 340, 348 and a network interface 330, 338, 346 to allow communications over network 326. The memory 332, 340, 348 is shown in FIG. 3 as including programming 334, 342, 350 that can control the processors 328, 336, 344. It should be understood that other devices that include computing systems can also include similar elements, such as a processor, network interface, memory, and computer programming.

In some embodiments, the system server 320, the subject testing device 318, and the regulatory device 322 can take the form of or include a standard computer system, or, in some embodiments, can take the form of or include a mobile device, such as a smartphone or tablet computer. The devices 320, 322 can actually be implemented using a plurality of separate, individual computers.

A standard computer system can operate application software or browser software, such as programs 334, 342, 350, which can be stored in memory 332, 340, 348 on the respective devices. The programs can allow the devices to communicate over the network 326 as part of the system 364.

In particular, the programming 334, 350 can at least allow communication with the system server 320 over the network 326. In other embodiments, the system 364 will be designed to allow direct communication between the regulatory device 322 and the subject testing device 318.

In various embodiments, the system server 320 receives data from a subject testing device 318 in the form of testing data or test events, and stores it in the database 324. In various embodiments, the system server 320 receives data from a regulatory device 322 in the form of criteria data and/or requests for data. The criteria data (discussed below) can be saved in the database 324, such as a stringency database.

The system server 320 can be in communication with a plurality of other subject testing devices 318 and may aggregate all their data in a single database 324. In other embodiments, data from separate subject testing devices 318 can remain separated into separate databases 324 that are still accessible to the system server 320. In various embodiments, the system server 320 can allow multiple regulatory devices 322 to access data from multiple subject testing devices 318.

The computer of devices 320, 322 can be a computing device that includes a processor for processing computer programming instructions. In most cases, the processor can be a CPU. Various different CPU devices are possible, such as those created by Intel Corporation (Santa Clara, California), Advanced Micro Devices, Inc (Santa Clara, California), or a RISC processor produced according to the designs of Arm Holdings PLC (Cambridge, England). Additionally, the computers can include memory. The memory can be in the form of both temporary, random access memory (RAM) and more permanent storage such a magnetic disk storage, FLASH memory, or another non-transitory (also referred to as permanent) storage medium. The memory and storage, which can be referred to collectively as "memory", can contain both programming instructions and data. In various embodiments, both programming and data can be stored permanently on non-transitory storage devices and transferred into RAM when needed, such as for processing or analysis. In some embodiments, the computers can include a graphics processing unit (or GPU) for processing of visual input and outputs.

In various embodiments, the various data can be stored locally and/or stored remotely. In FIG. 3, the data can be stored in database 324. In many embodiments, the database 324 can be a portion of the system server 320. In other embodiments, the database 324 can be a separate element from the system server 320. In some embodiments, the database 324 can consist of local storage on the various devices included in the system 364.

In various embodiments, the database 324 can include defined database entities that, in some embodiments, can constitute database tables in a relational database. In other embodiments, entities may represent database objects or any other type of database entity usable with a computerized database. In various embodiments, the phrase database entity can refer to data records in a database, which can include a row in a database table, an instantiation of a database object, or any other populated database entity. Data within this database 324 can be "associated" or "linked" with other data. This association can be implemented in a variety of techniques depending on the technology used to store and manage the database, such as through formal relationships in a relational database or through established relationships between objects in an object-oriented database.

Database 324 can include a plurality of jurisdiction profiles 352, such as one profile 352 for each jurisdiction. Database 324 can include control data 354, such as one for each device 318. The jurisdiction profile 352 can include criteria data 356 and contact data 358. The criteria data 356 can include the requirements or configurations for a plurality of various control requirements for the given jurisdiction. The contact data 358 can include data related to how or where reporting of testing data, violation data, or summary data from the system 364 to the jurisdiction should be sent.

The control data 354 can be subject test device 318 specific. Each subject test device 318 can be configured to the requirements of one or more jurisdictions. In various embodiments, the subject test device 318 is configured to the requirements of one jurisdiction (the most stringent jurisdiction). In such embodiments, the reports sent to each jurisdiction can be configured to comply to the requirements of the jurisdiction that the specific report is being sent to. As an example, a first jurisdiction can have an alcohol concentration limit of 0.02% and a second jurisdiction can have an alcohol concentration limit of 0.015%. The subject test device can be configured to the requirements of the second jurisdiction, because the second jurisdiction's requirements are more stringent. As a result, the alcohol concentration limit can be set at 0.015%. If the subject provides a sample with an alcohol concentration of 0.017%, the subject test device can prevent the vehicle from starting. Further, a report including a potential violation or including the test event data can be sent to the second jurisdiction, whereas a report to the first jurisdiction would not include this test event as a potential violation because the measured alcohol concentration was below the first jurisdiction's requirement of 0.02%.

In various embodiments, the concentration limits for different substances can be different. As an example, in some embodiments, the alcohol concentration limit can be set as 0.02%, whereas a tetrahydrocannabinol (THC) concentration limit can be set as 0, such that any detectable amount can result in a violation or the inability to start a vehicle. Alternatively, both an alcohol concentration limit and a THC concentration limit can have a non-zero value.

The control data 354 can include operating data 360 and criteria data 362. The criteria data 362 can be the settings or requirements for the multiple control requirements for the given device 318. The criteria data 362 can be the criteria data 356 from a controlling or primary jurisdiction. In some embodiments, the criteria data 362 is a hybrid or combination of criteria data 356 from two or more different jurisdictions.

In various embodiments, the database 324 can further include a plurality of subject profiles 361, such as one subject profile for each subject that has been issued a subject testing device. The subject profile 361 can include a subject identifier 363. The subject identifier 363 can include information for identifying the subject or other personal information, such as the subject's name, address, email address, phone number, birthdate, driver's license number, identification number, or the jurisdiction that issued his/her driver's license. The subject profile 361 can further include monitoring jurisdictions 365, such as the identity of one or more jurisdictions that are requiring the subject to use the subject testing device. The subject profile 361 can also include compliance device data 367, such as data identifying the type of subject testing device and/or an identification number of the subject testing device that has been issued to the subject. The subject profile 361 can further include compliance information, such as when the subject was issued the compliance device, rental or lease information regarding the compliance device, or payment/fee status. System 364 can include the transfer and receival of various portions of data between the various devices and components of the system 364.

In some embodiments, the database 324 can further include a testing database 369. In some embodiments, the testing database 369 can include test event data. Test event data can be created by the subject testing device in response to a testing event. The test event data can be received from the subject testing devices 318. In various embodiments, the subject testing device 318 can create test event data for each test event. In some embodiments, the test event data is stored within the user profile 361 for the subject that is associated with the test event data. In some embodiments, the user profiles 361 can be stored in the testing database 369. In other embodiments, the user profile 361 is linked with the test event data within the testing database 369, such as to identify which subject the test event data is associated with.

Figure 4:
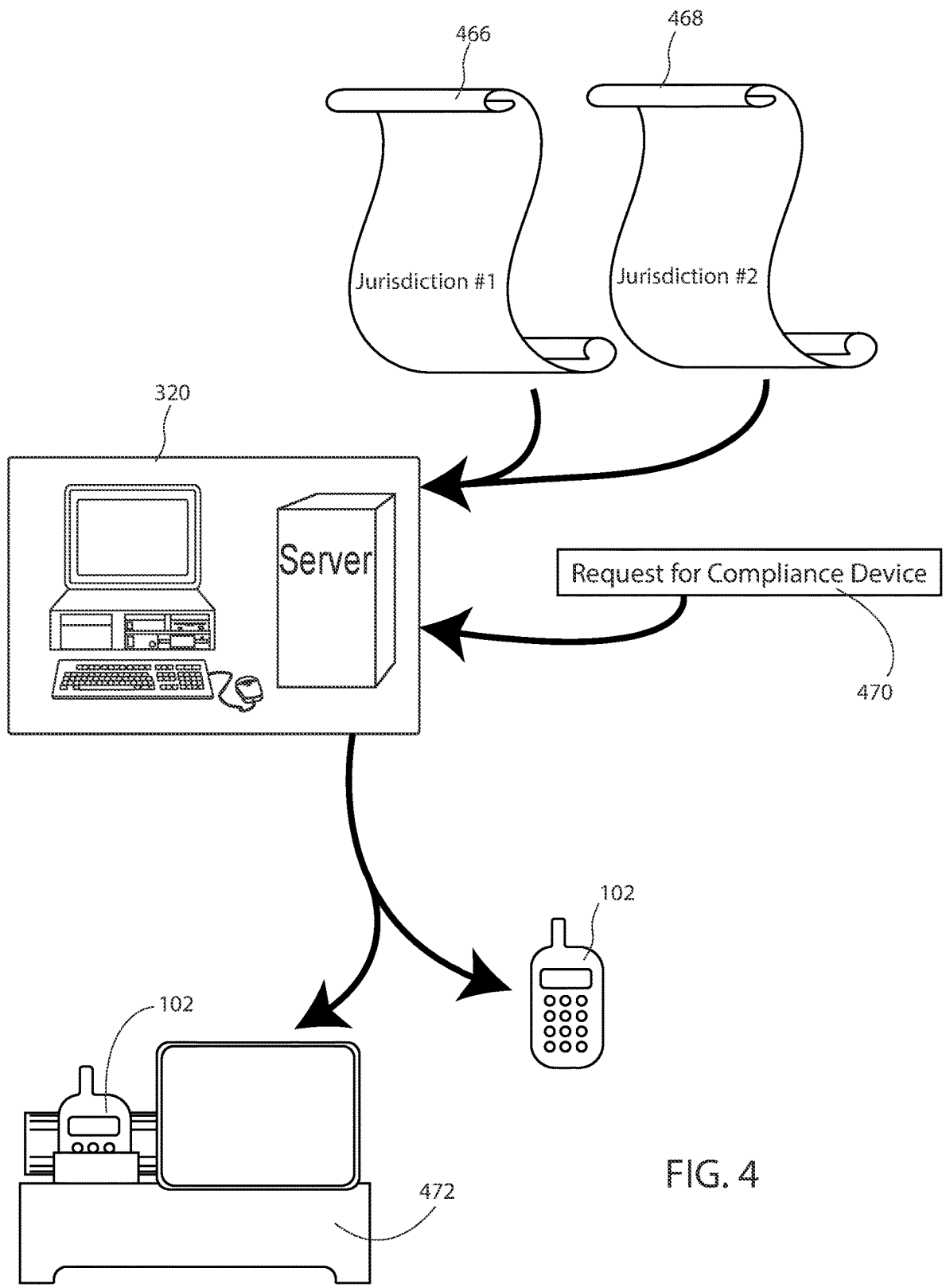
FIG. 4 is a schematic view of various components of a system in accordance with various embodiments herein.

FIG. 4 is a schematic of various data flows within the system in accordance with various embodiments herein. In various embodiments, the system server 320 can receive criteria data from one or more jurisdictions 466, 468. In various embodiments, at least a portion of the criteria data can be statutory requirements of the given jurisdiction 466, 468.

After receiving the criteria data from the jurisdictions 466, 468, the system server 320 can receive a request for a compliance device 470 from a subject. The request for a compliance device 470 can include a request that the provided device ensures that the subject is compliant for at least two jurisdictions, such as jurisdictions 466, 468. In some embodiments, the compliance device 470 can be compliant with at least two jurisdictions, at least three jurisdictions, at least four jurisdictions, at least five jurisdictions or even more than five jurisdictions depending on the needs of the subject.

Upon determining which jurisdictions the requested compliance device needs to be configured for, the system server can analyze the various criteria data from the jurisdictions to determine what the controlling pieces of criteria data should be.

After determining the controlling pieces of criteria data, the system server 320 can send the necessary instructions to the compliance device or subject testing device (e.g. detection unit 102 or control system 104). Upon receiving the controlling pieces of criteria data, the device can be programmed or configured as needed to meet the determined requirements. In various embodiments, the device can be configured to the requirements of the most stringent jurisdiction.

In various embodiments, the system server 320 can electronically send instructions for preparing a subject testing device (compliance device) in accordance with the criteria data and/or a control requirement frame of the more stringent jurisdiction 466, 468. In various embodiments, the system server 320 can electronically send instructions for preparing the subject testing device in accordance with the criteria data and/or the control requirement frame as a combination of criteria data from multiple jurisdictions 466, 468.

The system server 320 can prepare firmware for the subject testing device in accordance with the criteria data and/or the control requirement frame of the more stringent jurisdiction.

In various embodiments, the system server 320 can electronically send the firmware to the subject testing device directly. In some embodiments, the system server 320 can electronically send the firmware to the subject testing device through a transfer device, such as a calibration station 472.

In various embodiments, the calibration station 472 can be configured, in part, to calibrate the alcohol detection element of the BAIID 100. In some embodiments, the calibration station 472 can expose the alcohol detection element to a reference gas including a known concentration of alcohol. The BAIID 100 can be adjusted or configured to ensure that the BAIID 100 is providing accurate results of alcohol concentration of the sample it is provided. Various calibration stations are disclosed in U.S. Pat. No. 10,663,440, titled "SECURE DATA HANDLING IN A BREATH ALCOHOL CALIBRATION STATION," issued on May 26, 2020, which is hereby incorporated by reference in its entirety and U.S. Pat. No. 10,877,008, titled "REFERENCE GAS MANAGEMENT IN A BREATH ALCOHOL CALIBRATION STATION" issued on Dec. 29, 2020, which is hereby incorporated by reference in its entirety.

Figure 5:
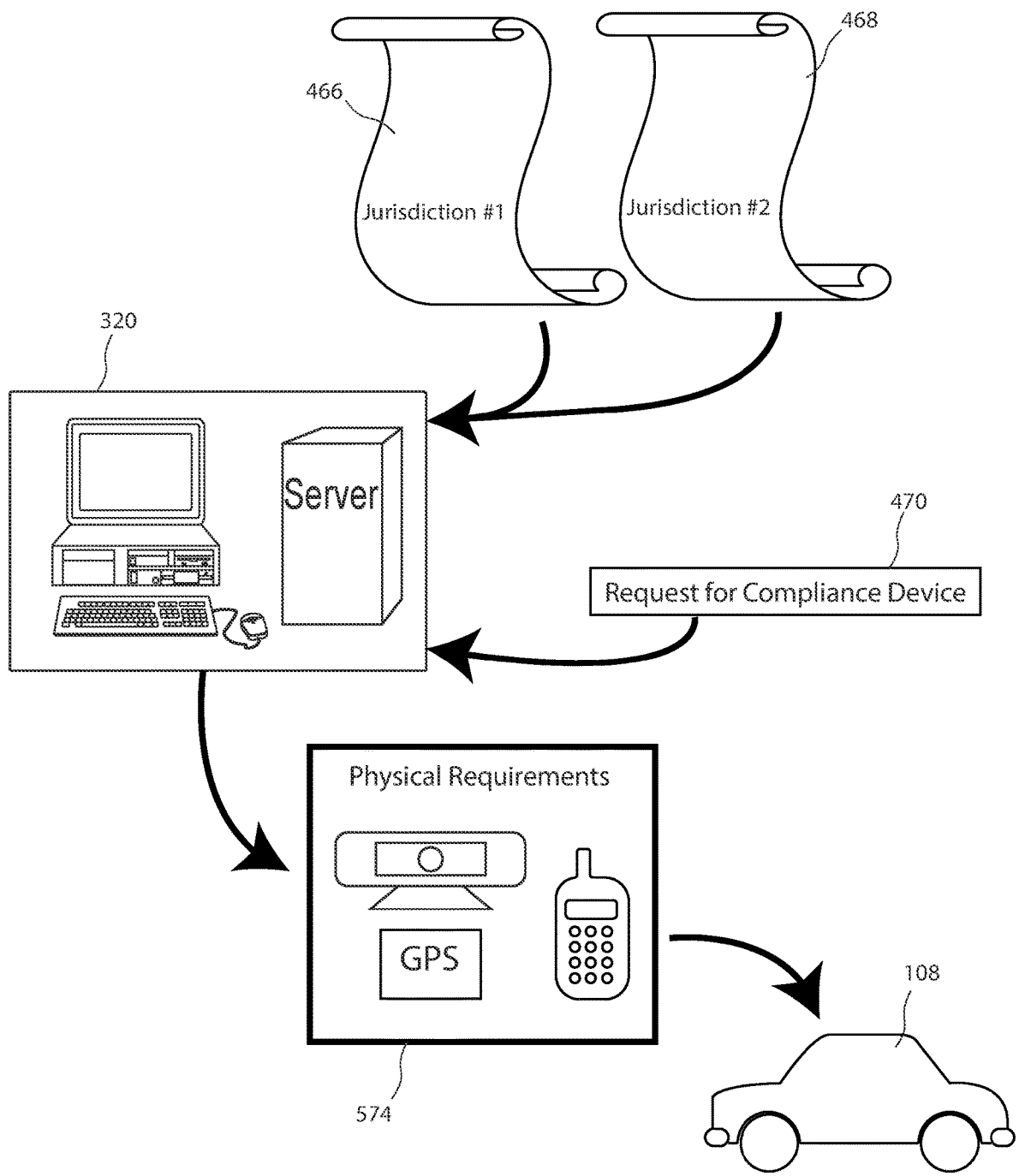
FIG. 5 is a schematic view of various components of a system in accordance with various embodiments herein.

FIG. 5 shows a similar schematic of data flows as FIG. 4. However, instead of the firmware being updated in the subject test device, the output is data related to the physical requirements 574 of the system. In FIG. 4, instructions can be sent to the subject testing device. The instructions can be related to how the device operates. As an example, the subject testing device can receive a blood alcohol content threshold for the subject to start the vehicle, such an instruction can be a portion of the firmware installed on the subject testing device.

In addition to providing instructions for how the device should operate, the system server 320 can also determine what the physical requirements 574 of the subject testing device should be as shown in FIG. 5. After the physical requirements 574 are determined, the components can be installed in a vehicle 108. In some embodiments, the physical requirements 574 can include what components are required, such as a camera, a GPS, and the type of alcohol testing element. In various embodiments, the system server 320 can send order data to a shipping device. The order data can include the physical requirements for the subject testing device. The shipping device can order and have the device shipped to a service center where the subject testing device can be installed into the subject's vehicle 108.

Figure 6:
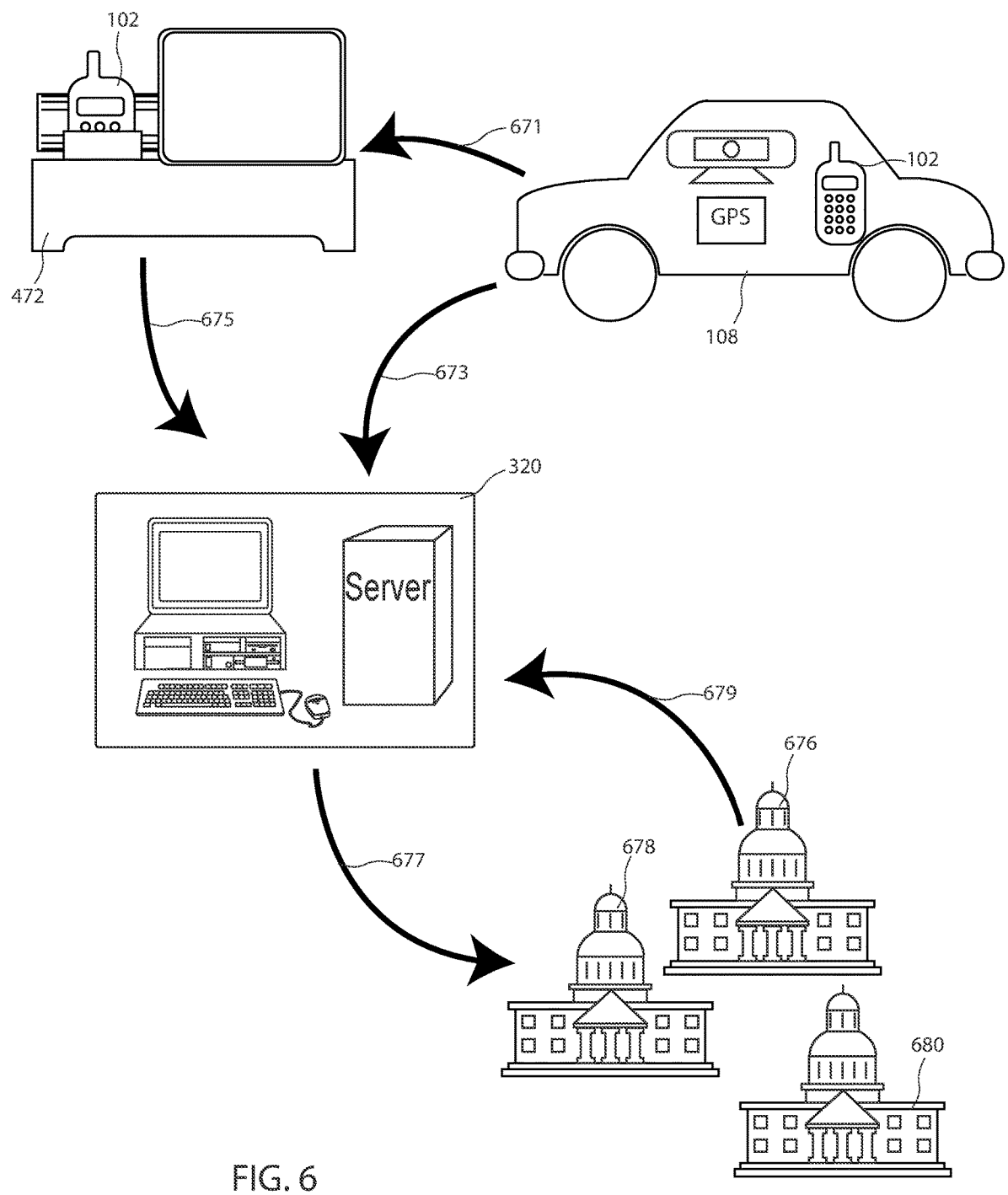
FIG. 6 is a schematic view of various components of a system in accordance with various embodiments herein.

FIG. 6 shows a schematic of the subject testing device in use and transferring data to other portions of the system in accordance with various embodiments herein. The subject testing device including the detection unit 102 can record and save testing data in response to a testing event. A testing event can be defined as anytime the system requests the subject to provide a sample or anytime the subject provides a sample. In many cases, the subject will provide a sample in response to a request/prompt from the system, this situation can result in a test event and testing data being created and saved. In various embodiments, the testing data can include one or more of the following: a time of when the testing event occurred, a date of when the testing event occurred, the location of the testing event, the alcohol (or other substance) concentration of the sample provided, an image of the sample being provided, the number of miles traveled since the last test event, when the vehicle was started, when the vehicle was stopped, and any potential violation that might have occurred.

In various embodiments, the system server 320 can receive the testing data from the subject testing device. In some embodiments, the system server 320 can directly receive the testing data from the subject testing device (as shown by arrow 673), such as when the subject testing device includes a cellular modem for connecting to the network 326. In other embodiments, a portion of the subject testing device can be connected to or inserted in a transfer device, such as a calibration station 472. FIG. 6 shows the detection unit 102 being removed from the vehicle 108 and inserted into the calibration station 472 (depicted with arrow 671). In various embodiments, the detection unit 102 can require routine calibration, such as to ensure the detection unit 102 is accurately measuring the alcohol content in the provided sample. In some embodiments, the transfer device (in this embodiment, in the form of a calibration station 472) can include the necessary hardware and software to connect to the network 326. The transfer device can transfer data, such as the testing data, from the subject testing device to the system server 320, such as shown by arrow 675 in FIG. 6.

In various embodiments, the system server 320 can prepare a report for each jurisdiction that the subject is being monitored by. The report can include reporting data for each jurisdiction. The reporting data can include at least a portion of the testing data, such as when test events occurred and the results of the test events. The system server 320 can send reports (e.g. report data) to one or more jurisdictions 676, 678, 680, such as by sending (represented by arrow 677) the report data to a regulatory device 322 associated with each jurisdiction 676, 678, 680.

In some embodiments, instead of the system server 320 sending data to the jurisdictions 676, 678, 680, the jurisdictions 676, 678, 680 can access the data on the system server 320, such as through a web-based portal (as shown by arrow 679). The regulatory device 322 can access a report or other data that is stored on the system server 320 through network 326.

In some embodiments, the system server can prepare a first report and a second report. The first report and the second report can include different data. As an example, a first jurisdiction can have a BrAC threshold of 0.02 for a failed test and a second jurisdiction can have a BrAC threshold of 0.015 for a failed test. If a subject has a BrAC for a test event of 0.017, the test event would not fail for the first jurisdiction, but it would fail for the second jurisdiction. As a result, a first report sent to the first jurisdiction or accessed by the first jurisdiction would not include a violation for this test event. However, a second report sent to the second jurisdiction or accessed by the second jurisdiction would include a violation for this test event. The system server 320 can prepare reports that are jurisdiction specific.

In another example, a first jurisdiction can require location data to be included in the testing data, such as data from a GPS system associated with the subject testing device, while a second jurisdiction does not require location data. A report sent to (or accessed by) the first jurisdiction can include the location data, while a second report sent to (or accessed by) the second jurisdiction can exclude the location data.

In some embodiments, a first report sent to or accessed by the first jurisdiction can include some common test data or other data as a second report sent to or accessed by the second jurisdiction. Further, in some embodiments, the first report can also include or exclude data that is or is not present in the second report, such that the first report and the second report can differ from each other. In some embodiments, identical reports can be sent to or accessed by multiple jurisdictions.

In some embodiments, the system server 320 can automatically send a report to a jurisdiction, such as at a set time interval or at a set triggering event. As an example, the set time interval could be once a week, once every other week, once a month, or once every other month. As an example, the set triggering event could be every time the system server receives test data from the subject testing device, every time the system determines a violation based on review of the test data, or in response to a request from a jurisdiction (through the regulatory device). In various embodiments, the different jurisdictions can have different time intervals or different triggering events. In some embodiments, instead of sending a report to a jurisdiction, the system server 320 can send a prompt noting that a new report has been prepared. The jurisdiction, through the regulatory device, can access the report by logging into the web-based portal to access the report.

FIG. 7 shows a schematic of a matrix or algorithm 782 that includes criteria data from various different jurisdictions in accordance with various embodiments herein. In various embodiments, each jurisdiction can have its own requirements that a subject must adhere to as part of their monitoring process.

Each jurisdiction can have a control requirement frame 784, 786, 788, 790, 792, 794, 796, 798. The control requirement frame can include the jurisdiction's requirements. Each control requirement frame 784, 786, 788, 790, 792, 794, 796, 798 can include criteria data for a plurality of control requirements 704, 708, 712, 716, 720, 724 or sub frames. The criteria data can be the specific requirement for each control requirement. The system server 320 can receive the criteria data from the jurisdictions, such as receiving a first control requirement frame 784 from a first jurisdiction, a second control requirement frame 786 from a second jurisdiction, a third control requirement frame 788 from a third jurisdiction and so on for each jurisdiction. The system server 320 can receive the criteria data from the jurisdictions. In some embodiments, the system server 320 can directly receive the criteria data from a computing device associated with a jurisdiction, such as the computing device sending criteria data to the system server 320. In other embodiments, the system server 320 can receive criteria data from the jurisdictions though user input. A user can review the criteria data of a jurisdiction and manually input the criteria data to the system server 320. The system server 320 can also receive criteria data from the jurisdictions through a scrubbing process. In some embodiments, the system server 320 can be configured to routinely access a database, website or other reference related to a jurisdiction.

Each criteria data can be sorted, scored, or ranked 706, 710, 714, 718, 722, 726 relative to other criteria data for the same control requirement. In various embodiments, the criteria data can be sorted, scored, or ranked based on the stringency or restrictiveness of the criteria data. Shown in the example of FIG. 7, the higher the score for a portion of criteria data, the more restrictive the portion of criteria data is. The scores for each of the portions of criteria data can be compiled into a total score 728 to determine which jurisdictions are the strictest, most stringent, or most restrictive. In some embodiments, the compiled score or total score 728 can be impacted by an adjustment variable. The adjustment variable can be used to increase the level of stringency for a jurisdiction based on requirements that the jurisdiction has, but that are not relevant to or required by other jurisdictions. As an example, a jurisdiction can have a requirement that no matter the circumstances, in order to fulfill the requirements of the jurisdiction, the device must be configured exactly the jurisdiction's requirements. As another example, a jurisdiction can require a cellular modem to contact emergency services if a subject has an alcohol concentration over a threshold, whereas no other jurisdictions might have this requirement.

In some embodiments, the system can receive a request for a device that complies with the control requirement frame of a single jurisdiction. The device can be configured to the requirements of the jurisdiction's control requirement frame.

In some embodiments, the system can receive a request for a device that complies with the control requirement frames of two or jurisdictions, or the system can receive a request to add the requirements of a second (or more) jurisdiction to an already in-use device. In response, the system can access the ranked control frames of the requested jurisdictions. The system can determine the control requirement frame for the more stringent jurisdiction, such as based on the total score 728 (shown in FIGS. 8 and 9), or in other embodiments, the system can provide a hybrid of jurisdictional requirements (shown in FIG. 10), such as configuring the device for the more stringent criteria data for each control requirement. In some embodiments, after determining the controlling set of criteria data 702 the device will need to be configured to, the system can notify a compliance user of the control requirement frame or the set of criteria data that the device will be configured to. In other embodiments, the system can configure a subject testing device to the criteria data (shown in FIG. 4) or output the physical requirements needed (shown in FIG. 5).

FIG. 8 shows a schematic of a matrix or algorithm 882 that includes criteria data from various different jurisdictions in accordance with various embodiments herein. The algorithm can include a plurality of control requirement frames 884, 886, 888, 890, 892, 894, 896, 898. Each control requirement frame can include criteria data for a plurality of control requirements, or sub frames, 804, 808, 812, 816, 820, 824. Each portion of criteria data can be sorted, scored, or ranked 806, 810, 814, 818, 822, 826 relative to other criteria data for the same control requirement. A total score 828 can be determined for each control requirement frame. A group of controlling criteria data 802 can be established.

In some embodiments, the system can determine which jurisdiction is the most stringent or most restrictive, and the system can configure the subject test device to that jurisdiction's requirement. The jurisdiction that the device is configured to can be referred to as the primary jurisdiction.

In various embodiments, the control requirements can include an alcohol (or other intoxicant) concentration limit 804, physical requirements (GPS 808, camera 812, etc. . . . ), calibration requirements (service location 816, number of dirty samples 820, reporting of service technician/personnel 824, etc. . . . ), servicing requirements, and/or reporting requirements (data of test events, location of test events, all test events or just potential violations, etc. . . . ). The control requirements can include requirements or settings for a device. The control requirements can include operating requirements, such as what constitutes a failed test or what data needs to be collected during operation. The control requirements can include physical requirements, such as what elements or portions of the system are needed to comply with the jurisdiction's requirements. The control requirements can include calibration requirements, such as requirements related to maintaining a device, how often the device needs to be calibrated, or how the device needs to be calibrated. The control device can include reporting requirements, such as requirements of what needs to be reported to a jurisdiction. The report to a jurisdiction can include various portions of information or data, such as test event data. The report to a jurisdiction can include summaries or conclusions based on the test event data, such as a note of a violation or a potential violation.

FIG. 8 shows an example where the two jurisdictions requested for compliance are Alabama and California. The controlling data can be set to the control requirement frame for California. California is a stricter jurisdiction. Further, fulfilling the requirements of California will meet the requirements of Alabama. California and Alabama can still receive two different reports. As an example, if the subject has a BAC of 0.023, a violation can be included in the report to California, but a violation will not be in the report to Alabama.

FIG. 9 shows a schematic of a matrix or algorithm 982 that includes criteria data from various jurisdictions in accordance with various embodiments herein. The algorithm can include a plurality of control requirement frames 984, 986, 988, 990, 992, 994, 996, 998. Each control requirement frame can include criteria data for a plurality of control requirements, or sub frames, 904, 908, 912, 916, 920, 924. Each portion of criteria data can be sorted, scored, or ranked 906, 910, 914, 918, 922, 926 relative to other criteria data for the same control requirement. The total score 928 can be determined for each control requirement frame. A group of controlling criteria data 902 can be established.

FIG. 9 shows an example where the two jurisdictions requested for compliance are Alabama and Colorado. The controlling data can be set to the control requirement frame for Colorado. Colorado is a stricter jurisdiction. Generally fulfilling the requirements of Colorado will meet the requirements of Alabama. However, Colorado only requires one dirty sample to be used during calibration compared to Alabama requiring two dirty samples. In such instances, the system can contact the non-primary or non-controlling jurisdiction, in this case Alabama, to obtain approval for an exception. In some embodiments, the system can send a request to a regulatory device of the non-primary jurisdiction requesting the exception. In some embodiments, when the non-primary jurisdiction approves of the exception, the exception can be stored in the database 324, such that if another device is requested to comply with the requirements of Alabama and Colorado, the system can automatically approve of the exception based on the previous guidance. As such, the controlling requirements can be set to those of the control requirement frame of Colorado.

Similar to FIG. 8, Colorado and Alabama can receive two different reports. As an example, if the subject has a BAC of 0.023, a violation can be included in the report to Colorado, but a violation will not be in the report to Alabama.

FIG. 10 shows a schematic of a matrix or algorithm 1082 that includes criteria data from various jurisdictions in accordance with various embodiments herein. The algorithm can include a plurality of control requirement frames 1084, 1086, 1088, 1090, 1092, 1094, 1096, 1098. Each control requirement frame can include criteria data for a plurality of control requirements, or sub frames, 1004, 1008, 1012, 1016, 1020, 1024. Each portion of criteria data can be sorted, scored, or ranked 1006, 1010, 1014, 1018, 1022, 1026 relative to other criteria data for the same control requirement. The total score 1028 can be determined for each control requirement frame. A group of controlling criteria data 1002 can be established.

In various embodiments, the set of controlling criteria data 1002 or operational control data can be a hybrid that includes data from more than one control requirement frame. In some embodiments, the criteria data within each subframe can be ranked based on the relative stringency of criteria data. Upon receiving a request for a compliance device according to the requirements of the first jurisdiction and the second jurisdiction, the system can access the ranked criteria data within each subframe of the requested jurisdictions. The system can then determine the control criteria data 1002, which can include portions of more than one control requirement frame. The control criteria data 1002 can be established on a subframe-by-subframe basis, such that the most stringent criteria data of the selected jurisdictions for each subframe can be set as the controlling data for that subframe. In various embodiments, the frame provided to the compliance device can be an operational control frame or a combined control frame.

FIG. 10 shows an example, similar to FIG. 9, where the two jurisdictions requested for compliance are Alabama and Colorado. The controlling data 1002 can be mostly set to the control requirement frame for Colorado, since Colorado is generally a stricter jurisdiction.

However, Alabama is stricter for at least one subframe. Alabama requires at least two dirty samples used during calibration, whereas Colorado only requires one. The controlling criteria data for the number of dirty samples during calibration 1020 can be set as two. As a result, the requirements for Alabama and Colorado will both be met by the controlling data 1002. The controlling data 1002 can include a hybrid of control requirement frames. The controlling data 1002 can include at least a portion of the criteria data of at least two different control requirement frames. Similar to the embodiments of FIGS. 8 and 9, Colorado and Alabama can receive two different reports.

Figure 11:
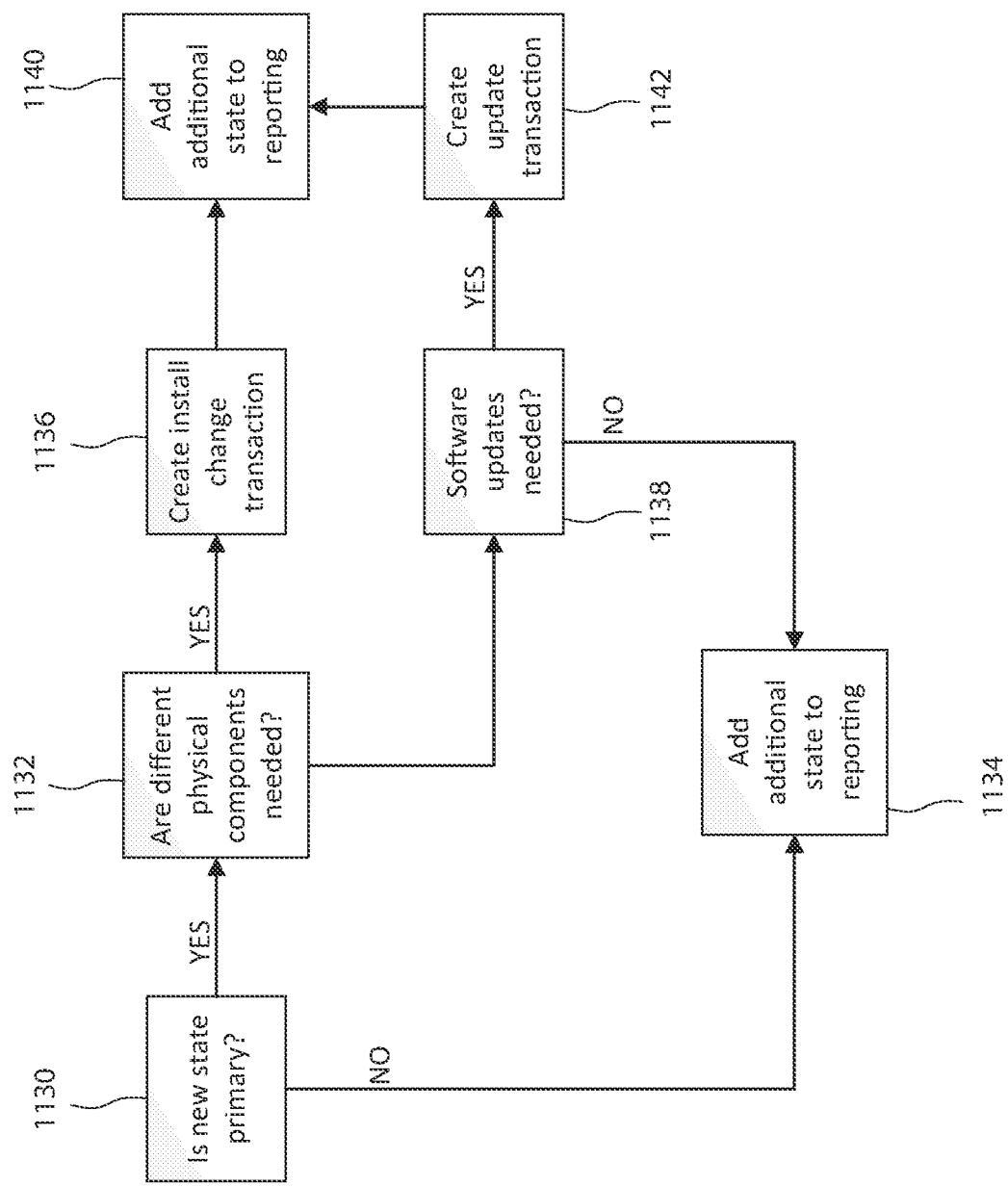
FIG. 11 is a flowchart depicting various steps in accordance with various embodiments herein.

FIG. 11 shows a flowchart depicting various steps in accordance with various embodiments herein. In some embodiments, a device can already be programmed, installed, and in use, when the subject requests that the device have an additional jurisdiction added to their monitoring situation. The system can determine if the new jurisdiction is going to be the primary state or if the new state will change the requirements of the device 1130. If the addition of the new state does not affect the requirements of the device, the additional state can be added to the reporting requirements 1134.

If changes are needed to the device, the system can determine if new physical components are required 1132. If new physical requirements are needed, an install change transaction 1136 can be created, such as sending notification data to the subject, ordering new physical requirements, sending new physical requirements to a service center, or scheduling an appointment for the subject at a service center. Further, the additional state can be added to the reporting requirements 1140.

If new physical requirements are not required, the system can determine if new software or firmware updates are needed 1138. If they are not needed, the additional state can be added to the reporting requirements 1134. If they are needed, the system can create an update transaction 1142. The update transaction 1142 can include sending software or firmware updates directly to the subject testing device, scheduling an appointment for the subject at a service center, or sending software or firmware updates to a transfer device, such as a calibration station. Further, the additional state can be added to the reporting requirements 1140.

A user can be required to use a monitoring device for a set time period, such as three months, six months, or one year. In various situations, different jurisdictions can have different time period requirements for a user. As an example, a first jurisdiction can require a user to have a device for at least 180 days, and a second jurisdiction can require the user to have a device for 90 days. In various situations, the starting day can be different for different jurisdictions. As an example, a first jurisdiction can require a user to have a device starting on January $1^{st}$, and a second jurisdiction can require a user to have a device starting on February $1^{st}$. A device can be configured to be updated to the requirements of a controlling jurisdiction throughout the use of the device by the user depending on which jurisdictions the device needs to comply with and/or report to.

As an example, the user can have a device according to the criteria data for a first jurisdiction starting on January $1^{st}$. The first jurisdiction can require the user to continue using the device through June $30^{th}$. On February $1^{st}$, the user can start fulfilling a requirement for a second jurisdiction that requires the user to start using the device according to the criteria data of the second jurisdiction until May $1^{st}$. The systems and methods described herein can provide a device that is acceptable to both jurisdictions. The device can be configured to the criteria data of the first jurisdiction from January $1^{st}$ through January $31^{st}$. On February $1^{st}$ the device can be updated to comply with the criteria data of the second jurisdiction (assuming the second jurisdiction is stricter than the first jurisdiction). The device can continue operating according to the criteria data of the second jurisdiction through May $1^{st}$. On May $1^{st}$, the user no longer needs to comply with the requirements of the second jurisdiction. The device can be updated (either through remote means or through an update at a transfer device) according to the criteria data of the first jurisdiction. The primary jurisdiction or the controlling jurisdiction can vary and be modified as needed over time according to the needs of the user.

Computer System

Figure 12:
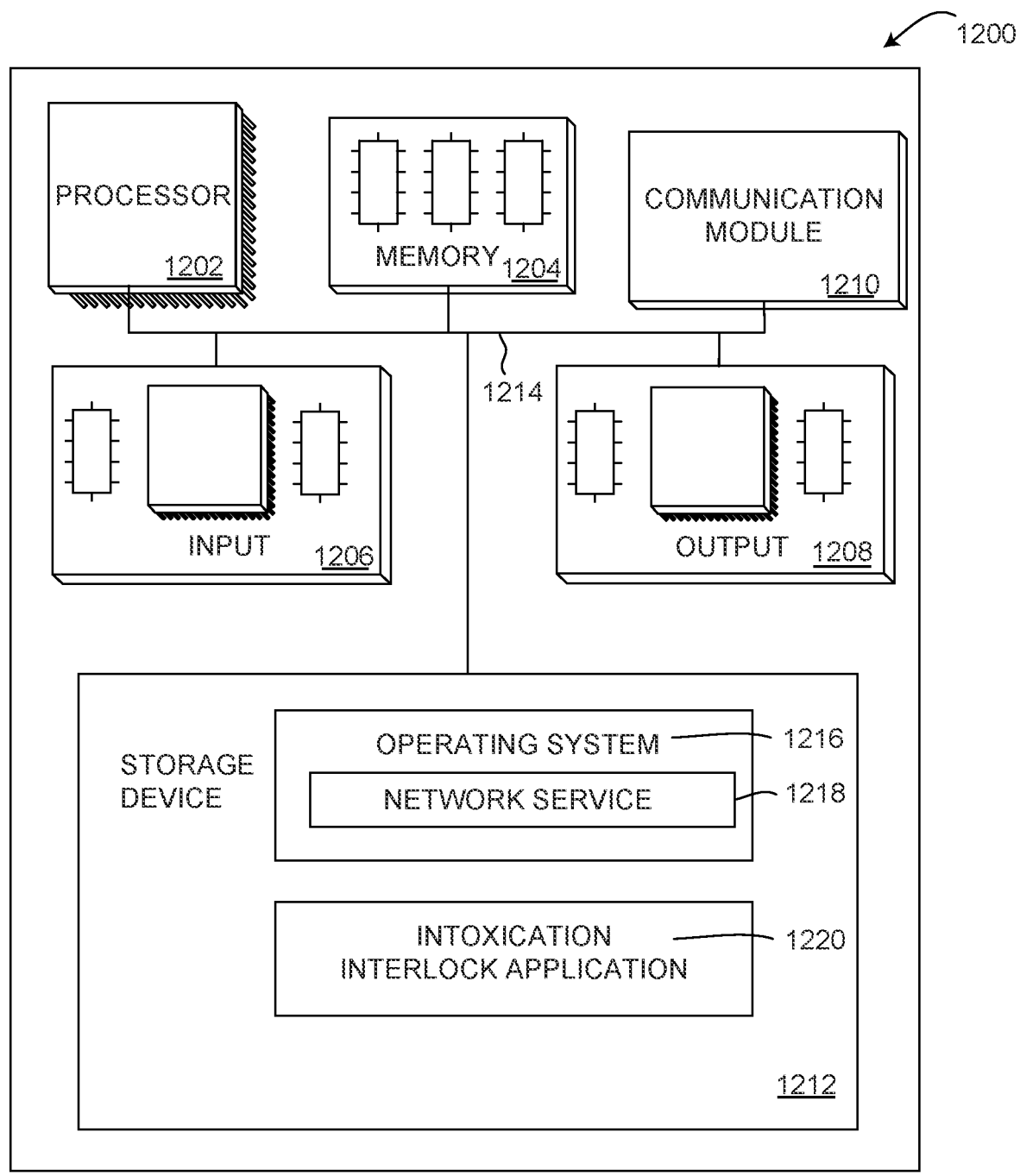
FIG. 12 is a schematic of a computer system in accordance with various embodiments herein.

Referring now to FIG. 12 a computer system is shown in accordance with various examples herein. FIG. 12 illustrates one example of a computing device 1200, but it should be understood that additional computing devices 1200 may be used in other embodiments, such as discussed in regard to FIG. 3. Although computing device 1200 is shown as a standalone computing device, computing device 1200 may be any component or system that includes one or more processors or another suitable computing environment for executing software instructions in other examples and need not include all of the elements shown here. A portion of a subject testing device, such as a control system, a wireless relay system, and a detection unit as described herein are examples of components that can be implemented using computing devices such as computing device 1200. In other embodiments, the regulatory device 322 and/or the system server 320 can include a computer system 1200.

As shown in the embodiment of FIG. 12, computing device 1200 includes one or more processors 1202, memory 1204, one or more input devices 1206, one or more output devices 1208, one or more communication modules 1210, and one or more storage devices 1212. Computing device 1200, in one example, further includes an operating system 1216 executable by computing device 1200. The operating system includes in various examples services such as a network service 1218. One or more applications, such as an intoxication interlock application 1220 are also stored on storage device 1212 and are executable by computing device 1200.

Each of components 1202, 1204, 1206, 1208, 1210, and 1212 may be interconnected (physically, communicatively, and/or operatively) for inter-component communications, such as via one or more communications channels 1214. In some examples, communication channels 1214 include a system bus, network connection, inter-processor communication network, or any other channel for communicating data. Applications such as intoxication interlock application 1220 and operating system 1216 may also communicate information with one another as well as with other components in computing device 1200.

Processors 1202, in one example, are configured to implement functionality and/or process instructions for execution within computing device 1200. For example, processors 1202 may be capable of processing instructions stored in storage device 1212 or memory 1204. Examples of processors 1202 include any one or more of a microprocessor, a controller, a digital signal processor (DSP), an application specific integrated circuit (ASIC), a field-programmable gate array (FPGA), or similar discrete or integrated logic circuitry.

One or more storage devices 1212 may be configured to store information within computing device 1200 during operation. Storage device 1212, in some examples, is known as a computer-readable storage medium. In some examples, storage device 1212 comprises temporary memory, meaning that a primary purpose of storage device 1212 is not long-term storage. Storage device 1212 in some embodiments includes a volatile memory, meaning that storage device 1212 does not maintain stored contents when computing device 1200 is turned off. In other embodiments, data is loaded from storage device 1212 into memory 1204 during operation. Examples of volatile memories include random access memories (RAM), dynamic random-access memories (DRAM), static random-access memories (SRAM), and other forms of volatile memories known in the art. In some examples, storage device 1212 is used to store program instructions for execution by processors 1202. Storage device 1212 and memory 1204, in various embodiments, are used by software or applications running on computing device 1200 such as intoxication interlock application 1220 to temporarily store information during program execution.

Storage device 1212, in some examples, includes one or more computer-readable storage media that may be configured to store larger amounts of information than volatile memory. Storage device 1212 may further be configured for long-term storage of information. In some examples, storage devices 1212 include non-volatile storage elements. Examples of such non-volatile storage elements include magnetic hard discs, optical discs, floppy discs, flash memories, or forms of electrically programmable memories (EPROM) or electrically erasable and programmable (EEPROM) memories.

Computing device 1200, in some examples, also includes one or more communication modules 1210. Computing device 1200 in one example uses communication module 1210 to communicate with external devices via one or more networks, such as one or more wireless networks. Communication module 1210 may be a network interface card, such as an Ethernet card, an optical transceiver, a radio frequency transceiver, or any other type of device that can send and/or receive information. Other examples of such network interfaces include Bluetooth, 3G, 4G, 5G, Wi-Fi radios, and Near-Field Communications (NFC), and Universal Serial Bus (USB). In some examples, computing device 1200 uses communication module 1210 to wirelessly communicate with an external device such as via public network such as the Internet.

Computing device 1200 also includes in one example one or more input devices 1206. Input device 1206, in some examples, is configured to receive input from a user through tactile, audio, or video input. Examples of input device 1206 include a touchscreen display, a mouse, a keyboard, a voice responsive system, video camera, microphone, or any other type of device for detecting input from a user. Sensors, such as temperature sensors or vibration sensors, can also be included in the device 1200 or communicate with the device 1200 to provide information to a processor. For example, a vibration sensor or temperature sensor can be configured to provide information about a vehicle engine, such as whether or not it is running. A wireless transceiver can act as an input device 1206 when it is configured to provide feedback confirming that instructions are received or actions are executed.

One or more output devices 1208 may also be included in computing device 1200. Output device 1208, in some examples, is configured to provide output to a user using tactile, audio, or video stimuli. Output device 1208, in one example, includes a display, a sound card, a video graphics adaptor card, or any other type of device for converting a signal into an appropriate form understandable to humans or machines. Additional examples of output device 1208 include a speaker, a light-emitting diode (LED) display, a liquid crystal display (LCD), or any other type of device that can generate output to a user.

Computing device 1200 may include operating system 1216. Operating system 1216, in some examples, controls the operation of components of computing device 1200, and provides an interface from various applications such intoxication interlock application 1220 to components of computing device 1200. For example, operating system 1216, in one example, facilitates the communication of various applications such as intoxication interlock application 1220 with processors 1202, communication unit 1210, storage device 1212, input device 1206, and output device 1208. Applications such as intoxication interlock application 1220 may include program instructions and/or data that are executable by computing device 1200. As one example, intoxication interlock application 1220 may include instructions that cause computing device 1200 to perform one or more of the operations and actions described in the examples presented herein.

Although specific embodiments have been illustrated and described herein, any arrangement that achieve the same purpose, structure, or function may be substituted for the specific embodiments shown. This application is intended to cover any adaptations or variations of the example embodiments of the invention described herein. These and other embodiments are within the scope of the following claims and their equivalents.

Detection Unit Options

Throughout the application, a detection unit having a detection element has been described. In some embodiments, the detection unit can be a part of a vehicle immobilization system. In some embodiments, the detection unit can be a part of a monitoring system, such as a portable monitoring system or an at-home monitoring system. In various embodiments, the detection unit can be configured to receive a biological sample from a user. In some embodiments, the biological sample can include a breath sample, a blood sample, a saliva sample, a sweat sample, or a urine sample.

The detection unit has sometimes been described as an alcohol breath detector which a user blows into, causing the breath sample to enter a fuel cell detector element. In alternative methods and systems, different detection units and detection elements can be used.

For example, instead of or in addition to a fuel cell detection element, the system can include one or more of a complementary metal oxide semiconductor (CMOS) sensor, a metal oxide semiconductor (MOS) sensor, a semiconductor sensor, and an infrared (IR) sensor.

In some examples, detection elements can be used that provide a continuous signal. Detection elements for alcohol that can provide a continuous signal are a complementary metal oxide semiconductor (CMOS) sensor, a metal oxide semiconductor (MOS) sensor, a semiconductor sensor, and an infrared (IR) sensor. These detection elements and detection elements that provide a continuous signal do not need to wait for a predetermined time period after receiving a gas sample to provide a gas alcohol content reading that is considered accurate. In contrast, fuel cell detection elements operate on a fixed volume gas sample when measuring alcohol content.

In other examples, instead of testing a user's breath for alcohol, the detection unit can test the user's breath for *cannabis* (i.e. tetrahydrocannabinol), opioids, or other intoxicants. In other examples, instead of testing the user's breath for an intoxicant, the detection unit can be a transdermal device that is in contact with the user's skin and detects a level of alcohol, *cannabis*, opioids, or other intoxicants in a user. Transdermal sensors can be part of a wrist-worn device, an ankle-worn device, a device attached to another part of the user's body, or a device embedded in a steering wheel or another part of the vehicle. If a transdermal unit is used as the detection unit, then instead of prompting the user to provide a breath sample, the system can ask the user to bring the detection unit into contact with the user's skin. If the detection unit is already in contact with the user's skin, then the system can simply take the measurement and determine if there is an intoxicant present above a threshold.

These alternatives for a detection unit and a detection element can be used with each of the systems described herein instead of the breath detection element that is otherwise described. The systems and methods presented here may be implemented in part using a computerized device, such as a smartphone, handheld, or other computerized device.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

As used herein, the recitation of numerical ranges by endpoints shall include all numbers subsumed within that range (e.g., 2 to 8 includes 2.1, 2.8, 5.3, 7, etc.).

The headings used herein are provided for consistency with suggestions under 37 CFR 1.77 or otherwise to provide organizational cues. These headings shall not be viewed to limit or characterize the invention(s) set out in any claims that may issue from this disclosure. As an example, although the headings refer to a "Field," such claims should not be limited by the language chosen under this heading to describe the so-called technical field. Further, a description of a technology in the "Background" is not an admission that technology is prior art to any invention(s) in this disclosure. Neither is the "Summary" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A method, comprising:
 a. receiving, at a non-transitory computer memory, criteria data regarding a first control requirement frame for a first jurisdiction, a second control requirement frame for a second jurisdiction, and a third control requirement frame for a third jurisdiction, wherein the criteria data comprises for each of the control requirement frames at least:
  i. criteria data for an intoxicant concentration limit data subframe;
  ii. criteria data for a calibration requirement data subframe; and
  iii. criteria data for a reporting subframe;
 b. storing the criteria data in a stringency database;
 c. sorting the first, second and third control requirement frames based on the relative stringency of criteria data,
 d. receiving a request for a compliance device according to the requirements of the first jurisdiction and the second jurisdiction, wherein the compliance device comprises an ignition interlock device;
 e. accessing the sorted control frames of the first and second jurisdictions to determine an operational control frame based on the sorted control frames;
 f. providing the operational control frame, and
 g. receiving test event data from the compliance device in response to a testing event, wherein the testing event comprises the compliance device prompting a user to provide a sample.

2. The method of claim 1, wherein sorting the first, second and third control requirement frames comprises evaluating the intoxicant concentration limit data subframes relative to each other, evaluating the calibration requirement data subframes relative to each other, and evaluating the reporting subframes relative to each other.

3. The method of claim 1, wherein the criteria data for each control requirement frame comprises a compliance device service location subframe or a compliance device service personnel subframe.

4. The method of claim 1, further comprising electronically sending instructions for preparing the compliance device in accordance with the operational control frame.

5. The method of claim 1, further comprising preparing firmware for the compliance device in accordance with the operational control frame.

6. The method of claim 5, further comprising electronically sending the firmware to the compliance device.

7. The method of claim 5, further comprising electronically sending the firmware to a transfer device, wherein the transfer device is configured to configure the firmware of the compliance device.

8. The method of claim 7, wherein the transfer device comprises a calibration station, wherein the calibration station is configured to calibrate the compliance device and communicate with a non-transitory computer memory of the compliance device.

9. The method of claim 1, wherein the intoxication concentration limit data is selected from the group consisting of an alcohol concentration limit, a tetrahydrocannabinol (THC) concentration limit, and an alcohol concentration limit and a tetrahydrocannabinol (THC) concentration limit.

10. The method of claim 1, wherein the ignition interlock device comprises a breath alcohol ignition interlock device.

11. The method of claim 1, further comprising:
i. receiving test event data from the compliance device in response to a testing event.

12. The method of claim 11, further comprising:
j. preparing a first report for one of the at least two jurisdictions, comprising a common portion of the test event data and a unique portion of the test event data;
k. preparing a second report for a second of the at least two jurisdictions comprising the common portion of the test event data, wherein the second report does not include the unique portion of the test event data so that the first report differs from the second report; and
l. sending the first report to at least one of the jurisdictions; and
m. sending the second report to at least one of the jurisdictions.

13. The method of claim 12, wherein the testing event data comprises an intoxicant concentration value from a biological sample provided to the compliance device.

14. The method of claim 13, wherein the biological sample comprises a breath sample, a saliva sample, a blood sample, or a urine sample.

15. The method of claim 1, wherein the compliance device is configured to receive a biological sample, and wherein the compliance device is further configured to analyze the biological sample and to determine an intoxicant concentration.

16. The method of claim 1, wherein providing the operation control frame comprises sending hardware data to a remote computing device, wherein the hardware data is defined by the operational control frame.

17. The method of claim 16, wherein the hardware data comprises instructions for preparing the compliance device.

18. A method, comprising:
a. receiving, at a non-transitory computer memory, criteria data regarding a first control requirement frame for a first jurisdiction, a second control requirement frame for a second jurisdiction, and a third control requirement frame for a third jurisdiction, wherein the criteria data for each control requirement frame comprises at least:
 i. criteria data for an alcohol concentration limit data subframe;
 ii. criteria data for a calibration requirement data subframe; and
 iii. criteria data for a reporting subframe;
b. storing the criteria data in a stringency database;
c. sorting the criteria data within each subframe based on the relative stringency of criteria data;
d. receiving a request for a compliance device that complies with the first jurisdiction and the second jurisdiction, wherein the compliance device comprises an ignition interlock device;
e. accessing the sorted criteria data within each subframe of the first and second jurisdictions to determine control criteria data for a combined control requirement frame for the compliance device, wherein the control criteria data comprises the criteria data of a more stringent jurisdiction for each subframe, wherein the control criteria data comprises at least a portion of the criteria data for the first jurisdiction and a portion of the criteria data for the second jurisdiction;
f. providing the combined control requirement frame for the compliance device, and
g. receiving test event data from the compliance device in response to a testing event, wherein the testing event comprises the compliance device prompting a user to provide a sample.

19. A system, comprising:
a non-transitory computer memory and a computer processor, and computer instructions stored on the memory for instructing the processor to perform the steps of:
a. receiving, at the non-transitory computer memory, criteria data regarding a first control requirement frame for a first jurisdiction, a second control requirement frame for a second jurisdiction, and a third control requirement frame for a third jurisdiction, wherein the criteria data for each control requirement frame comprises at least:
 i. criteria data for an intoxicant concentration limit data subframe;
 ii. criteria data for a calibration requirement data subframe; and
 iii. criteria data for a reporting subframe;
b. storing the criteria data in a stringency database;
c. sorting the first, second and third control requirement frames based on the relative stringency of criteria data,
d. receiving a request for a compliance device according to the requirements of the first jurisdiction and the second jurisdiction, wherein the compliance device comprises an ignition interlock device;
e. accessing the sorted control frames of the first and second jurisdictions to determine an operational control frame based on the sorted control frames;
f. providing the operational control frame, and
g. receiving test event data from the compliance device in response to a testing event, wherein the testing event comprises the compliance device prompting a user to provide a sample.

* * * * *